US007083820B2

(12) United States Patent
Schilling et al.

(10) Patent No.: US 7,083,820 B2
(45) Date of Patent: Aug. 1, 2006

(54) METHOD FOR PRODUCING BIOLOGICALLY ACTIVE PRODUCTS

(76) Inventors: Marvin L. Schilling, 3201 S.O. #16, Fort Smith, AR (US) 72903; Richard D. Fafard, 5410 Highland Dr., Fort Smith, AR (US) 72903

( * ) Notice: Subject to any disclaimer, the term of this patent is extended or adjusted under 35 U.S.C. 154(b) by 667 days.

(21) Appl. No.: 09/964,120

(22) Filed: Sep. 25, 2001

(65) Prior Publication Data

US 2002/0065231 A1 May 30, 2002

Related U.S. Application Data

(60) Provisional application No. 60/237,005, filed on Sep. 29, 2000.

(51) Int. Cl.
| | |
|---|---|
| *A23B 4/03* | (2006.01) |
| *A23P 1/00* | (2006.01) |
| *A61K 9/14* | (2006.01) |
| *A61K 35/12* | (2006.01) |
| *A61K 35/34* | (2006.01) |

(52) U.S. Cl. ...................... 426/465; 426/665; 426/443; 426/455; 424/489; 424/520; 424/548

(58) Field of Classification Search ................ 426/665, 426/422, 424, 425, 437, 443, 455, 465; 435/41, 435/408; 424/480, 404, 489, 439, 520, 548
See application file for complete search history.

(56) References Cited

U.S. PATENT DOCUMENTS

| | | | | | |
|---|---|---|---|---|---|
| 3,878,197 | A | * | 4/1975 | Maret | 260/236.5 |
| 4,066,083 | A | * | 1/1978 | Ries | 424/400 |
| 4,250,139 | A | * | 2/1981 | Luck et al. | 422/21 |
| 4,404,033 | A | * | 9/1983 | Steffan | 106/124.3 |
| 4,789,497 | A | * | 12/1988 | Uneo et al. | 252/194 |
| 5,562,535 | A | * | 10/1996 | Puppolo | 452/198 |
| 5,645,851 | A | * | 7/1997 | Moore | 424/439 |
| 5,773,241 | A | * | 6/1998 | Ericsson | 435/41 |

FOREIGN PATENT DOCUMENTS

| | | | | |
|---|---|---|---|---|
| DE | 202800 | | * | 10/1983 |
| EP | 288405 | | * | 10/1988 |
| GB | 2144865 | A | * | 3/1985 |
| JP | 59025637 | | * | 2/1984 |
| JP | 59025637 | A | * | 2/1984 |
| JP | 59-088065 | | * | 5/1984 |
| JP | 359088065 | | * | 5/1984 |
| JP | 02028119 | | * | 1/1990 |

* cited by examiner

*Primary Examiner*—Sreeni Padmanabhan
*Assistant Examiner*—S. Gollamudi
(74) *Attorney, Agent, or Firm*—Bernd W. Sandt

(57) ABSTRACT

The present invention relates to a process for dehydrating naturally occurring organic materials which contain a biologically active component, and in particular proteins, which does not change the original structure of the active component, by drying such material in particulate form in the presence of an antimicrobial agent and preferably an ionizable salt at temperatures at or below which denaturization occurs until the water content of the material is reduced to less than 15%.

10 Claims, No Drawings

METHOD FOR PRODUCING BIOLOGICALLY ACTIVE PRODUCTS

This application is a continuation in part of application 60/237,005 filed Sep. 29, 2000.

The present invention relates to a process for producing biologically active products which are safe for human consumption as well as for consumption by other life forms. More specifically the present invention relates to a method of stabilizing naturally occurring substances through dehydration without destroying the efficacy of such natural substances. Processing is done using hypertonic conditions, creating plasmolysis to microorganisms, while protesting the substance. The reduced water activity (Aw) at the final product ensures a wholesome product.

BACKGROUND OF THE INVENTION

There are a large number of naturally occurring substances that have found applications in various fields that must be processed to be suitable as a commercial product. Historically, maintaining the biological activity of certain potentially useful substances along with presenting this to the intended recipient in a safe manner, particularly regarding pathogen safety and the control of deleterious enzyme activity, is costly and frequently results in a decrease of the efficacy as a result of denaturing of the biologically active material. There are several commercial fields that market products based on naturally occurring biologically active products, such as in the pharmaceutical and dietary supplement fields, food field, medical field, over-the-counter medicine field, and the cosmetic field. The process of the present invention can be adapted to uses in all of these fields.

One example of an application of the process of this invention is in the preparation of type II collagen intended for arthritis sufferers. This compound is reported to work with the arthritis sufferer's immune system in a positive manner. As disclosed in the patents of Dr. Eugene Moore (U.S. Pat. Nos. 5,570,144, 5,529,786, 5,637,321 and 5,645,851), it is clear that for the type II collagen to be effective it must be prepared in a manner that is closest to its native state. Moore's suggested delivery of this material to the consumer, however, involves the retention of significant amounts of water, thus making the product susceptible to pathogen cross-contamination.

In the over-the-counter medicine field, willow bark was first chewed to lower fever and reduce pain as early as 400 BC, as suggested by Hippocrates. Because of a number of problems in making the product widely available including storing, handling and distributing the product, a chemist working in Germany in 1898, Felix Hoffman, synthesized and stabilized the active ingredient in willow bark, acetylsalicylic acid, known today as aspirin. The present invention, when applied to the dehydration of willow bark, produces a stable material that can be more effective than synthesized aspirin.

In the food field, a margarine-like spread is now available in supermarket dairy cases that contain plant stanol esters. These esters, derived from oilseed production, have been shown to reduce cholesterol. The process of this invention can be used to stabilize oilseed in a manner that is safe, effective, and easier to consume. Oil seed when treated in established ways to reduce enzymatic degradation can result in reduced efficacy.

In the pharmaceutical field, digitalis is a drug used to create a more effective heartbeat, and is a glycoside obtained from common foxglove leaves, classified as *Digitalis purea*. This process can be used to stabilize foxglove leaves in a manner that is safer and more effective and more affordable for the consumer.

In the medical field, Type 1, 3 and 5 collagens are known to be beneficial for skin health and are used to help wound healing. This process can be used to stabilize these collagens in a biologically active and safe form for use in wound healing while making the product more affordable to the consumer.

In the cosmetic field, many of the facial skin creams contain collagen. This process could be used to stabilize these collagens in a biologically more active and safe form.

Thus, irradiation, thermal processing, the use of preservatives, freeze drying and other known methods of sterilization, are either ineffective or difficult to use to stabilize a product for human consumption which retains the original biologic structure of naturally occurring materials. Accordingly, there is an acute need for novel method to retain the biologically active component in natural materials in its original form that can be delivered in a safe and cost-effective manner for human consumption and use by other life forms.

GENERAL DESCRIPTION OF THE INVENTION

The process of the present invention relates to the improved utility of naturally occurring substances of known beneficial effect which retain the original natural structure of such substances while eliminating microbial agents that can affect their quality and efficacy. This treatment comprises the dehydration and thus stabilization of naturally occurring substance at less than traditional processing temperatures in the presence of an antimicrobial component to reduce pathogenic load. The dehydration is preferably also carried out in the presence of an ionizable salt that is not harmful to the consumer in the concentrations employed. Other hypertonic agents, such as sugar or alcohol may also be used alone or in combination with the salt in certain applications. During and after processing, the salt acts as a further antimicrobial stabilizer against growth of pathogens and spoilage organisms during the process, which is oftentimes set at incubation temperatures for the organism of concern, and potential cross contamination.

One of the major features of this invention is that it provides a process that allows for using significantly less than traditional elevated temperatures for thermal processing to eliminate deleterious microbial agents and particularly pathogens, and therefore retains the biological state of the original product.

Another major feature of this invention is that the resulting product maintains its microbial safety for greater than 3 years at room temperature storage conditions. In addition, any deleterious enzyme activity is controlled, resulting in a more desirable commercially attractive product since enzymatic activity can bring about negative organoleptic properties, such as inappropriate odors. In addition, enzymatic activity can negatively affect the efficacy of a natural product.

The procedure of the present invention provides an improved economic method of converting naturally occurring substances to stable, consumable products that can also be used with other products, which heretofore have been treated with such things as chemical preservatives, thermal processing, irradiation, inert atmospheres, freeze drying, and other antimicrobial stabilization methods.

In the past, a consumable product would not be processed at the temperatures used in the present invention since the resulting products would be organoleptically unacceptable. The recent introduction of the dietary supplement business, where small amounts of material are allowed to be consumed, gives meaning to this invention. Not only are the products resulting from the process of the present invention stable and consumable for long periods, but in addition naturally occurring substances retain their natural original structure and thus complete efficacy contained in such substances. As a result improved products are obtained that are useful as dietary supplement, as pharmaceuticals, as over-the-counter medicines, as topical products in creams or lotions (such as a biologically active cream) in medical devices, such as biologically active bandages and as special ingredients in functional foods.

The process of the present invention is preferably used with proteins that have shown promise and usefulness as food supplements or a pharmaceuticals without denaturing the original structure of the protein and protecting the desirable synergism resulting from the interaction of the various protein species found in natural proteins.

DETAILED DESCRIPTION OF THE INVENTION

The process of the present invention comprises the dehydration of an organic substance under conditions which maintain the integrity and structure of the organic substance but still eliminates the majority of pathogens present and if desirable eliminate other microbes which cause spoilage, without substantially affecting the original structure of the substance. More specifically the process of the present invention involves heating a natural organic substance at temperatures below which denaturization occurs, and if desirable at reduced pressures, in the presence of an antimicrobial agent which can be an ionizable salt, but preferably is a combination of more effective antimicrobial agents and the ionizable consumable salt. The salt serves to protect the substance (plasmolysis conditions) from pathogen and spoilage organism growth during processing temperatures and as a stabilizing agent during and after processing to prevent deterioration of the dried product.

The materials used in this process can be any organic substance that contains sufficient water causing it to be subject to deterioration as a result of the action of light, enzymes and pathogens and spoilage organisms. The materials used in this process are materials that require stabilization during processing, storage, handling and distribution and consumption and/or use so that deleterious effects do not occur. The material is generally intended to be stored at room temperature, but can be usually also refrigerated and/or frozen, though generally not necessary.

The natural substances dehydrated by the process of the present invention can be any organic substance that contains sufficient water or the proper conditions to allow for the existence and growth of pathogens or other microbes and also substances that are subject to attack by deleterious enzymes. Thus proteins, lipids, e.g., fats, and carbohydrates are included as well as any other water containing biologically active substance. There is no need to purify the organic substances employed since the process can be employed with mixtures of organic substances. The addition of other additives either natural or synthetic such as coloring agents, lubricants and antioxidants does not take the products outside the scope of this invention.

However the process of the present invention finds particular utility in conjunction with the dehydration of proteins where it is desirable to maintain the original undenatured structure of the proteins and food materials which contain combinations of proteins which have a synergistic effect when consumed. For example chicken cartilage contains not only Type II collagen but in addition contains such proteins as glucosamine and chondroitin. As disclosed in the patents of Eugene Moore, U.S. Pat. Nos. 5,645,581, 5,637,321, 5,529,786 and 5,750,144 the use of undenatured Type II collagen reduces the symptoms of rheumatoid arthritis which may in part be due to the nature of the undenatured Type II collagen or the combination of such with other proteins present in chicken cartilage. In contrast denatured, purified Type II collagen does not provide the same type of relief or benefits as compared to the undenatured Type II collagen.

The stabilizing salt is an ionizable salt that is safe for consumption and in particular is either sodium or potassium chloride. Salt concentrations vary widely depending on the nature of the food material involved and the degree of stabilization desired. Thus it is generally possible to use lower concentrations of salt if the intent is to eliminate pathogens as distinguished from microbes which cause spoilage. Optimum or desirable concentrations can be established experimentally by aging the food material and observing the occurrence of an undesirable microbial load of pathogens. Excess amounts of salt do not prevent the dehydration but may affect the utility of the dehydrated material. In conjunction with the dehydration of proteins it is generally desirable to employ a concentration of about 15% based on the weight of the starting material which results in a concentration of about 45% in the dehydrated product.

The effect of the salt may be enhanced by the addition of an acid such as hydrochloric or acetic acid.

In general the process is conducted until the water content of the starting material is reduced to below 15% by weight and preferably into the range of 1 to 8%. No additional benefit results if the water concentration is reduced even further. At concentrations above 15% stabilization and elimination of the pathogens and other microbes may only be partial and inadequate to stabilize the material.

An antimicrobial chlorine-containing agent, such as sodium hypochlorite, alone or in combination with a suitable acid, such as hydrochloric acid, in solution is added to the starting material to further assist in reducing the initial microbial load. This is particularly the case where the material is also to be stabilized against microbes such as can cause spoilage. The useful concentration range of the chlorine agent in parts per million (ppm) is from 1 ppm to 10,000 ppm. Use range of the acid in pH is from pH 1 to pH 10. When using a chlorine agent it may be desirable to first soak the material in the chlorine agent before subjecting the material to the drying process.

The material to be dehydrated is generally comminuted so as to allow for even water removal and prevent wet spots in the interior of the particle. The ability to dehydrate evenly increases as the particle size is reduced. The particles, however, should not be reduced to a size where such will affect the structure of the material being dehydrated or cause excessive agglomeration. Particles are preferably in the range of 1 to 1000 mesh size.

A wide variety of commercially available drying equipment can be employed in the process of the present invention. Preferred equipment is such as permits uniform drying of the material without physically abrading the particles. Fluid bed or rotary drum dryers, which monitor temperature and moisture continuously, are particularly preferred. Release agents and other materials, which aid in the drying of the natural substances, may be added to the drying step.

Thus aids that help reduce agglomeration and coating of the walls of the dryer, such as lecithin and hydroxypropyl methylcellulose, are useful in the method of the present invention.

The present invention is particularly useful in preparing protein materials in stable form which retain their original structure and thereby their original therapeutic values. Type II collagen derived from chicken cartilage is a biologically active protein molecule when processed in a suitable manner. It is important to maintain the potency of this component as it can be readily lost by using many traditional stabilizing techniques when processing to stabilize and make safe, such as traditional thermal processing. It is well known that this component is deactivated when thermally processed. Such technology processes as irradiation and freeze drying processing may initially maintain the activity of this component, however regarding maintaining biological stability and safety after the process the existing technologies are quite inferior to this new method and this new method is significantly economically preferable. A significant issue is cross contamination after processing by the behavior of individuals who may handle or consume the product. This new method ensures that reasonably inappropriate behavior in this regard does not bring about an unsafe product. Also the material desired is processed around the same temperature as it functioned in its natural environment, ensuring that it maintains its native functional state. This is not possible using traditional processing since these temperatures are incubation temperatures for pathogens resulting in exponential growth of such and thereby an unwholesome product.

The biologically active components in a number of lifesaving drugs were originally isolated from plants by chemical processes that were slow and expensive and because of their treatment became subject to an extensive regulatory process. This new method can be used to maintain the biological activity of these phytochemicals at significantly reduced processing costs. These products being natural products can also be marketed in less time and cost due to less regulatory requirements. Because the original natural environment is maintained products obtained by the process of this invention provide outstanding efficacy at lower concentrations and after long storage.

Natural occurring biologically active ingredient include chondroitin and glucosamine that are components of such things as chicken cartilage and are biologically active when processed using the methods of this invention. The berry of the Rocky Mountain Juniper is biologically active when dehydrated using this method. Foxglove containing naturally occurring digitalis is biologically active when using this method. Sitka Mountain Ash is similarly biologically active when processed by this method.

The invention is further illustrated by the following examples.

EXAMPLE 1

This example demonstrates the microbial conditions and water activity conditions of chicken sternal cartilage, deboned chicken breast shells and mechanically separated chicken in a sterile laboratory environment.

Chicken sternal cartilage is harvested from healthy young (less than 60 days of age) chickens, obtained from a chicken processor. The analysis of this material yielded 82.0% moisture, 0.2% fat, 12.7% protein, 2.2% ash and 2.9% carbohydrates. Also, chicken deboned breast shells and mechanically separated chicken (MSC) was obtained from the same processor, but was not analyzed for proximate analysis.

These three materials were tested for antimicrobial activity and the effect of an antimicrobial agent (sodium hypochlorite). The products were submitted to a series of 3 steps (first before chlorination, second after chlorination and third after drying in a sanitized fashion at approximately 100° F.) in which microbial profiles were performed for each step and the water activity index measured after drying. Material was comminuted to approximately 1/16" to 1/8" pieces (step 1). The resulting particles were soaked in a 200 ppm solution of sodium hypochlorite (step 2) and drying time was approximately 3 days using a standard food dehydrator, internal heat disconnected and using an external source of heat to control the temperature. The following results were obtained:

|        | Aerobic Plate Count (APC) | Coliform | E. coli | Water Activity (Aw) |
|--------|---------------------------|----------|---------|---------------------|
| Sternum |                          |          |         |                     |
| Step 1 | 134 Colony Forming Units (CFU)/gram (g) | 1 CFU/g | ND | Not Available (NA) |
| Step 2 | Non-Detected (ND) | ND | ND | NA |
| Step 3 | Non-Detected | ND | ND | 0.243 |
| Shell  |                          |          |         |                     |
| Step 1 | 5300 CFU/g | 3 CFU/g | ND | Not Available (NA) |
| Step 2 | ND | ND | ND | NA |
| Step 3 | ND | ND | ND | 0.458 |
| MSC    |                          |          |         |                     |
| Step 1 | 354,000 CFU/g | 3500 CFU/g | 700 CFU/g | Not Available (NA) |
| Step 2 | ND | ND | ND | NA |
| Step 3 | ND | ND | ND | 0.227 |

Note:
All microbial testing methods in all examples were conducted using approved AOAC methods. Available water activity (Aw) index is a measure of the amount of water in a substance and gives an indication of the water concentration a microorganism, such as a pathogen like Salmonella or an enzyme requires for growth.

This example demonstrates that even using low temperature drying to preserve the original structure of the protein, a product safe for human consumption can be produced in a sanitized environment that does not take into consideration the possibility of cross-contamination encountered in a manufacturing environment and the potential for cross-contamination by handlers and the consumer after processing is not addressed.

EXAMPLE 2

Another batch of fresh sternums was obtained and tested for microbial condition. Results indicated APC(s) of 78,000 CFU/g and 57,500 CFU/g, Coliform(s) of 17 CFU/g and 5 CFU/g, *E. coli*(s) of 3 CFU/g and 35 CFU/g and *Salmonella*(s) both being positive for this pathogen. Given theses conditions the use of an antimicrobial agent alone would not be adequate to protect the protein from pathogens and enzyme attack after manufacture and during storage before consumption. Therefore, an ionic salt was incorporated into the comminuted sternum at a level of approximately 76% chicken sternums to 24% potassium chloride (KCl) and this was processed in a similar manner as to Example 1, incorporating the antimicrobial step. The finished product was tested re APC, Coliform, *E. coli, Salmonella*, and yeast/mold. All tests were negative.

The use of this salt did not adversely affect the organoleptic properties of the final product and the microbial profile of the finished product was wholesome. The finished product contained less than 10% moisture with an Aw of less than 0.5, providing for a stable product, regarding potential cross contamination issues during manufacturing, handling, storage, distribution and end-user activities. The presence of the salt also increased the water removal rate as compared to drying the material in the absence of the salt.

EXAMPLE 3

Example 2 was expanded by increasing the amount of KCl to an amount that would make it suitable for use as a dietary supplement (meet FDA daily value), as a Type II collagen biologically active material. Tests were run using a blend of about 56% chicken sternal cartilage and 44% KCl. A rotary drum apparatus, using automatic controls for temperature monitoring was used. An antimicrobial as described previously was used prior to processing and this material was comminuted as described above. Temperatures during processing did not exceed 110° F. More than twenty batches were prepared. Moisture contents ranged from a high of 3.9% to a low of 0.9% and Aw of a high of 0.437 and a low of 0.158. All batches were microbially tested and APC(s) ranged from a high of 270 CFU/g to a low of non-detectable. Coliform was not detected. *E. coli* was not detected. All *Salmonella* tests were negative. These results show that this invention produces a wholesome, consumer-friendly, and safe product.

EXAMPLE 4

The microbial profile over time as the material is being dried was established. Product was prepared as described in Example 1, except using an 85/15 sternum to KCl mixture instead of just the sternum. The following results were obtained:

| Duration (Hours) | APC* | Coliform | E. coli | Staph. Aureus | Salmonella | Yeast/Mold | Moisture |
|---|---|---|---|---|---|---|---|
| 0 | 43,000 | ND** | ND | ND | NEG*** | 60 | NA**** |
| 3 | 34,000 | ND | ND | ND | NEG | 20 | 68.9% |
| 6 | 11,200 | ND | ND | ND | NEG | 80 | 46.7% |
| 10 | 5,300 | ND | ND | ND | NEG | ND | 33.5% |
| 24 | 1,080 | ND | ND | ND | NEG | ND | 24.3% |
| 28 | 820 | ND | ND | ND | NEG | ND | 13.4% |
| 34 | 320 | ND | ND | ND | NEG | ND | 4.8% |
| 48 | 120 | ND | ND | ND | NEG | ND | 4.3% |

*All numbers in CFU/g, ND is Non detected (<10 CFU/g),*NEG is Negative, ****NA is Not Available The results show that this invention, when performed under the proper conditions, provides for proper microbial profiles over time as the product is processed. It is well known that chicken, along with many other biological materials, contains pathogens of concern to public health. This invention also addresses the concern of cross-contamination and produces a product that is biologically active as intended and is safe for use by the consumer. This despite the fact that, as is well known, temperatures of 110° F. allow for significant microbial growth, which is prevented using the method of the present invention.

EXAMPLE 5

It is well known that when chicken cartilage containing Type II collagen is subjected to conditions such as high temperature for stabilization purposes, that the Type II collagen molecule denatures and is rendered ineffective regarding the biological activity for the intended purpose.

This example demonstrates the ability of this invention to maintain the undenatured native and biologically active Type II collagen contained in the chicken sternal cartilage, along with microbial product safety and organoleptic properties over time. Product was prepared as in Example 4 using a mixture of 60% chicken sternal cartilage and 40% KCl. The resulting product was studied using four measures; (1) electron microscope (EM) qualification, (2) enzyme linked immunosorbent analysis (ELISA) for qualification and quantification, (3) sequential solubilization/precipitation collagenase specific enzyme analysis (S/PCSE) and, (4) proximate analysis.

EM testing validated that the product of the process of this invention maintains the intact, native, undenatured form regarding the Type II collagen fibrils within the natural chicken sternal cartilage. ELISA testing validated and verified that the product of the process of this invention works to maintain the biologically active Type II collagen for use as intended and can be used for quantification. S/PCSE further validated and verified that the process of this invention works to maintain the biologically active Type II collagen for use as intended and can be used for quantification. Proximate analysis of the finished product made by this invention confirmed all testing with regards to expected protein percent as compared to reported literature values.

Product produced by this invention was tested at zero time and compared to product stored at room temperature for more than one year. The tests demonstrate that the product is stable for more than a year.

| TIME | Proximate Analysis-Protein* | S/PCSE | ELISA | EM |
|---|---|---|---|---|
| Zero | 12.4% | 11.7% | NA | DETECTED |
| >1 Year | 11.5% | 10.4% | 12.3% | NA |

Note: NA-Not Available

For comparison purposes, fresh chicken sternal cartilage was subjected to a thermal process that could potentially be used to maintain the product's safety during processing (but not post-processing, due to potential cross contamination). Using S/PCSE analysis it was determined that although the fresh sternum showed about 8% active Type II collagen in this unstable shelf stability form, after thermally processing at 250° F. for 1 hour, S/PCSE results indicated that less than 1% (almost unmeasureable), if any, remained.

The following data regards the microbiological stability of the product produced by this invention:

| Time | APC* | Coliform | E. coli | Staph. Aureus | Salmonella | Yeast/Mold |
|---|---|---|---|---|---|---|
| Zero | ND | ND | ND | ND | ND | ND |
| >1 Year | ND | ND | ND | ND | ND | ND |

ND is Non-Detected

Organoleptically the product starts at day 1 of storage as a lightly tanned, light chicken aroma, with no off-odors. After greater than 1 year of storage, these conditions are the same.

It is concluded that this invention produces a microbially safe product when processing in the proper fashion, along with this invention maintaining the biologically, as intended, active form of Type II collagen.

EXAMPLE 6

Following the procedure of Example 5, product was prepared using 85 parts cartilage, 15 parts KCl and 5 parts 1 Molar hydrochloric acid and exposed to varying drying times.

| Duration (Hours) | APC* | Coliform | E. coli | Salmonella |
|---|---|---|---|---|
| 0 | 80 | ND** | ND | NEG*** |
| 11 | ND | ND | ND | NEG |
| 48 | 70 | ND | ND | NEG |
| 50 | 20 | ND | ND | NEG |

*All numbers in CFU/g,
**ND is Non detected (<10 CFU/g),
***NEG is Negative,
This example indicates that the use of an acid enhances microbial control, and allows for shorter drying times.

EXAMPLE 7

To a mixture of comminuted chicken cartilage and 15% KCl, prepared as described in Example 1, was added 5 parts of hydroxypropyl methylcellulose as a drying agent and 2 parts of lecithin as a flow agent. The mixture when dried in a rotating drum drier dried more evenly in a shorter time without sticking to the drum as compared to a mixture not containing these additives.

EXAMPLE 8

The mixture of comminuted chicken cartilage and KCl of Example 2 was dispersed in water and then soaked onto a cotton fabric. The resulting wet fabric was then dried as described in Example 1 to a water content below 10%. The cotton fabric is then used as a bandage to improve the healing of wounds.

EXAMPLE 9

Comminuted pineapple was mixed with 15% KCl and dried in accordance with the method of Example 2 to a water content of less than 10%. The resulting dried pineapple is free of pathogens and stable against enzyme degradation.

EXAMPLE 10

Willow bark is comminuted and dehydrated in accordance with the procedure of Example 2. The resulting product maintains the activity of the naturally occurring acetylsalicylic acid and combines such with the other beneficial ingredients contained in willow bark and is available as an over-the-counter remedy.

EXAMPLE 11

Foxglove leaves are comminuted, combined with an antimicrobial agent and 15% of KCl and then dehydrated at temperatures of 100° F. until the moisture content is below about 7%. The resulting product is useful as a digitalis remedy available as a pharmaceutical.

EXAMPLE 12

Rape seed is comminuted and then dehydrated according to the procedure of Example 2 to a water content below 10%. The resulting product is useful as an additive to foods to control cholesterol.

EXAMPLE 13

Aloe leaves are comminuted, combined with an antimicrobial agent and 20% KCl and then dehydrated using the procedure of Example 2. The resulting product can be used for either internal applications to increase the immune resistance and in topical applications to aid in the healing of wounds.

EXAMPLE 14

Pig cartilage separated from the bone, comminuted and then dehydrated by the procedure of Example 2. The resulting product contains collagen 1,3 and 5 in the original state and is useful in topical applications.

EXAMPLE 15

85 parts of chicken sternum, which contains a high percentage of Type II collagen, is blended with 15 parts of potassium chloride. 100 parts of this mixture is soaked in 300 parts of a solution containing 200 ppm of chlorine at 40° F. for two hours. This soaking step is repeated twice for a minimum of six hours total and the water is filtered off.

The Type II collagen containing blend is then repeatedly run through a grinder until the particle size is reduced to about 1/16". The resulting particulate is blended with additional 15 parts of potassium chloride and reground. The mixture is then placed in a rotary drum dryer and heated at 104° F. until the water content is reduced to about 5%. The resulting stabilized material is further ground to a mesh size of 70–100 and results in a free flowing particulate containing about 38% of protein and 60% of potassium chloride.

As can be seen from the foregoing description a variety of organic materials containing biologically-active components can be dehydrated without destroying the original structure of such components, thereby maintaining the efficacy of the active component. The foregoing examples are not to be construed as limiting the scope of this invention, which finds utility for products in pharmaceutical and medical fields, in dietary supplements, in herbal remedies sold over-the-counter, in the cosmetics industry and in general food items which contain biologically active ingredients that are to be retained in their original natural state.

The invention claimed is:

1. A method for the dehydration of Type II collagen containing cartilage in its natural form, which comprises,
    (a) combining said cartilage with an antimicrobial agent and at least 15% by weight of the cartilage of an ionizing salt,
    (b) heating the resulting mixture in particulate form at a temperature below which denaturizattion of the Type II collagen occurs until the water content is reduced to below 15% by weight of the cartilage, and
    (c) recovering a product containing the collagen II-containing protein of the cartilage in its original form and having a salt content of at leant 45% by weight of the cartilage.

2. The method of claim 1 wherein the ionizing salt is used in solid form.

3. The method of claim 1 wherein the heating is conducted at a temperature below about 110° F.

4. The method of claim 1 wherein the process is carried out in the presence of an oxygen containing antimicrobial agent and an ionizable consumable salt.

5. The method of claim 4 wherein anti-microbial agent is a hypochlorite.

6. The method of claim 1 wherein the salt is sodium or potassium chloride.

7. The process of claim 1 in which the salt concentration in the dried product is from 45 to 60% of the cartilage.

8. The method of dehydrating chicken cartilage containing Type II collagen in its natural form which comprises
    (a) comminuting said cartilage,
    (b) soaking the resulting product in an aqueous solution of an antimicrobial agent, and blending such with potassium or sodium chloride in a concentration of at least 15% by weight of the comminuted product,
    (c) dehydrating the resulting mixture in particulate form at temperatures below 110° F. until the water content of the mixture is reduced to below 10%, and recovering a product containing the Type II collagen of the chicken cartilage in its natural form and having a salt content of 45 to 60% by weight of the cartilage.

9. The method of claim 8 wherein the antimicrobial agent is a hypochlorite.

10. The process of claim 1 wherein the dehydration is carried out in the presence of hydroxypropyl methylcellulose or lecithin.

* * * * *